US012123888B2

(12) United States Patent
Christey et al.

(10) Patent No.: US 12,123,888 B2
(45) Date of Patent: *Oct. 22, 2024

(54) APPARATUS AND METHOD FOR PICKING BIOLOGICAL SAMPLE

(71) Applicant: Isolation Bio Inc., San Carlos, CA (US)

(72) Inventors: Peter Christey, San Carlos, CA (US); Alexander Hallock, Redwood City, CA (US)

(73) Assignee: Isolation Bio Inc., San Carlos, CA (US)

( * ) Notice: Subject to any disclaimer, the term of this patent is extended or adjusted under 35 U.S.C. 154(b) by 963 days.

This patent is subject to a terminal disclaimer.

(21) Appl. No.: 16/878,549

(22) Filed: May 19, 2020

(65) Prior Publication Data

US 2020/0278372 A1 Sep. 3, 2020

Related U.S. Application Data

(63) Continuation of application No. 15/788,772, filed on Oct. 19, 2017, now Pat. No. 10,712,356, which is a continuation-in-part of application No. 15/135,377, filed on Apr. 21, 2016, now Pat. No. 10,900,073.

(60) Provisional application No. 62/484,395, filed on Apr. 12, 2017, provisional application No. 62/299,088, filed on Feb. 24, 2016, provisional application No. 62/292,091, filed on Feb. 5, 2016, provisional application No. 62/150,677, filed on Apr. 21, 2015.

(51) Int. Cl.
| | |
|---|---|
| *G01N 35/10* | (2006.01) |
| *B01L 3/00* | (2006.01) |
| *B01L 3/02* | (2006.01) |
| *C12M 1/04* | (2006.01) |
| *C12M 1/26* | (2006.01) |
| *C12M 1/32* | (2006.01) |
| *C12Q 1/6853* | (2018.01) |
| *G01N 35/00* | (2006.01) |
| *G06T 7/73* | (2017.01) |

(52) U.S. Cl.
CPC ........ *G01N 35/1081* (2013.01); *B01L 3/5085* (2013.01); *C12M 23/12* (2013.01); *C12M 23/24* (2013.01); *C12M 33/04* (2013.01); *C12Q 1/6853* (2013.01); *G01N 35/00029* (2013.01); *G01N 35/00693* (2013.01); *G01N 35/1004* (2013.01); *G06T 7/74* (2017.01); *B01L 3/0244* (2013.01); *B01L 2200/025* (2013.01); *B01L 2200/0689* (2013.01); *B01L 2200/12* (2013.01); *B01L 2200/141* (2013.01); *B01L 2300/021* (2013.01); *B01L 2300/0636* (2013.01); *B01L 2300/0681* (2013.01); *B01L 2300/0829* (2013.01); *B01L 2300/0893* (2013.01); *B01L 2300/165* (2013.01); *G01N 2035/00148* (2013.01); *G06T 2207/10056* (2013.01); *G06T 2207/30024* (2013.01); *G06T 2207/30204* (2013.01); *G06T 2207/30232* (2013.01)

(58) Field of Classification Search
CPC ............. G01N 1/00; G01N 35/00; B01L 3/00
See application file for complete search history.

(56) References Cited

U.S. PATENT DOCUMENTS

| | | | |
|---|---|---|---|
| 4,634,676 A | 1/1987 | Sapatino | |
| 5,061,621 A | 10/1991 | Perlman | |
| 5,587,322 A | 12/1996 | Chrebet | |
| 5,858,770 A | 1/1999 | Perlman | |
| 5,882,922 A | 3/1999 | Tyndorf | |
| 6,083,724 A | 7/2000 | Lowenthal | |
| 6,103,479 A | 8/2000 | Taylor | |
| 6,174,673 B1 | 1/2001 | Short | |
| 6,474,181 B2 * | 11/2002 | Gilson | G01N 35/10 |
| | | | 73/864.25 |
| 6,509,168 B2 | 1/2003 | Croteau | |
| 6,592,819 B1 * | 7/2003 | Ogura | B01J 19/0046 |
| | | | 422/50 |
| 6,900,055 B1 | 5/2005 | Fuller | |

(Continued)

FOREIGN PATENT DOCUMENTS

| | | | | |
|---|---|---|---|---|
| EP | | 2805768 A1 | 11/2014 | |
| WO | WO-2005052582 A2 * | | 6/2005 | ............ B01L 3/5085 |

(Continued)

OTHER PUBLICATIONS

Croatt o et al., Clinical Microbiology and Infection 22:217-235 (Year: 2016).*
Greub et al., Clinical Microbiology and Infection 17:655-660 (Year: 2011).*
Khatri et al., High Throughput Phenotypic Analysis of *Mycobacterium tuberculosis* and *Mycobacterium bovis* Strains' Metabolism Using Biolog Phenotype Microarrays. Plos One 8(1) : e 52673 (Year: 2013).*

(Continued)

*Primary Examiner* — Ethan C Whisenant
(74) *Attorney, Agent, or Firm* — Yong Chen; Lin Sun-Hoffman; Liu Chen & Hoffman LLP

(57) ABSTRACT

A picking instrument for picking biological samples, such as microbial samples, includes a picking pin having a distal tip and three degrees-of-freedom and configured to move in x, y, and z directions. The picking instrument also includes a loading platform comprising a first area and a second area, the first area configured to accommodate and secure a microfabricated chip including a plurality of microwells. The picking pin is programmatically controlled to pick a sample contained in one or more selected microwells of the microfabricated chip and then transfer the sample to a predetermined location at the destination sample holder. Methods of operating the picking instrument, including calibrating the coordinates of the selected microwell(s) relative to a location of the picking pin, are also provided.

13 Claims, 6 Drawing Sheets

(56) References Cited

U.S. PATENT DOCUMENTS

| | | | |
|---|---|---|---|
| 6,951,714 B2 | 10/2005 | Giovannoni | |
| 6,972,183 B1 | 12/2005 | Lafferty | |
| 7,011,957 B2 | 3/2006 | Lewis | |
| 7,019,827 B2 | 3/2006 | Lafferty | |
| 7,195,872 B2 | 3/2007 | Agrawal | |
| 7,419,778 B2 | 9/2008 | Van Damme | |
| 9,228,933 B2 | 1/2016 | Joseph | |
| 9,327,298 B1* | 5/2016 | Sauter, Jr. | B05B 5/00 |
| 10,712,356 B2* | 7/2020 | Christey | G06T 7/74 |
| 10,900,073 B2* | 1/2021 | Blainey | C12M 23/12 |
| 2002/0172993 A1* | 11/2002 | Nautiyal | C12Q 1/045 435/34 |
| 2003/0072679 A1* | 4/2003 | Johnson | F16K 11/0743 422/63 |
| 2003/0082551 A1* | 5/2003 | Zarling | C12N 15/1079 435/6.16 |
| 2003/0152957 A1* | 8/2003 | Shinohara | G01N 33/54366 435/7.1 |
| 2004/0181342 A1* | 9/2004 | Zhou | G06T 7/66 702/22 |
| 2004/0213446 A1* | 10/2004 | Shams | G06T 7/0012 382/129 |
| 2005/0070005 A1 | 3/2005 | Keller | |
| 2005/0255445 A1 | 11/2005 | Van Damme | |
| 2005/0286547 A1 | 12/2005 | Scherze | |
| 2006/0051246 A1* | 3/2006 | Toi | G01N 35/1011 422/561 |
| 2007/0026516 A1 | 2/2007 | Martin | |
| 2007/0072187 A1 | 3/2007 | Blok | |
| 2007/0196856 A1* | 8/2007 | Dong | A61K 31/727 435/7.1 |
| 2008/0206831 A1 | 8/2008 | Coffey | |
| 2008/0207461 A1* | 8/2008 | Ermantraut | G01N 35/00029 506/30 |
| 2009/0298153 A1 | 12/2009 | Martin | |
| 2010/0021959 A1 | 1/2010 | Ingham | |
| 2011/0160067 A1* | 6/2011 | Sundstrom | C12Q 1/04 506/7 |
| 2011/0294208 A1 | 12/2011 | Allbritton | |
| 2012/0291872 A1* | 11/2012 | Brady | B01L 9/06 422/524 |
| 2013/0052649 A1 | 2/2013 | Lee | |
| 2013/0065795 A1 | 3/2013 | Allbritton | |
| 2013/0295551 A1 | 11/2013 | Eddington | |
| 2014/0130614 A1* | 5/2014 | Zeng | G01N 35/00584 73/863.01 |
| 2014/0227684 A1 | 8/2014 | Hindson | |
| 2015/0057163 A1 | 2/2015 | Rotem | |
| 2015/0118707 A1* | 4/2015 | Selvaganapathy | C12Q 1/04 435/34 |
| 2015/0141261 A1 | 5/2015 | Hunicke-Smith | |
| 2015/0185208 A1* | 7/2015 | Pinkowitz | G01N 21/78 435/288.7 |
| 2015/0204862 A1 | 7/2015 | Fan | |
| 2015/0299784 A1 | 10/2015 | Fan | |
| 2016/0122753 A1 | 5/2016 | Mikkelsen | |
| 2016/0244825 A1 | 8/2016 | Vigneault | |
| 2016/0245805 A1 | 8/2016 | Baer | |
| 2016/0250632 A1 | 9/2016 | Hong | |
| 2016/0264919 A1 | 9/2016 | Kabaha | |
| 2016/0312275 A1 | 10/2016 | Blainey et al. | |
| 2017/0159045 A1* | 6/2017 | Serber | G01N 35/00871 |
| 2017/0198275 A1 | 7/2017 | Lee | |
| 2017/0247652 A1 | 8/2017 | Goluch | |
| 2017/0307606 A1 | 10/2017 | Hallock | |
| 2017/0362554 A1 | 12/2017 | Martin | |
| 2017/0362569 A1 | 12/2017 | Valamehr | |
| 2017/0363545 A1 | 12/2017 | Halverson | |

FOREIGN PATENT DOCUMENTS

| | | |
|---|---|---|
| WO | WO2014028537 | 2/2014 |
| WO | WO2015031691 | 3/2015 |
| WO | 2015172025 A1 | 11/2015 |

OTHER PUBLICATIONS

Hanif et al. Isolation and characterization of a β-propeller gene containing phosphobacterium *Bacillus subtilis* strain KPS-11 for growth promotion of potato (*Solanum tuberosum* L.). Frontiers in Microbiology 6:583 (Year: 2015).*

Extended European Search Report on EP17862455, dated Sep. 1, 2020 (Year: 2020).*

Canadian Office Action on CA 3,057,965, mailed on Feb. 14, 2024.

International Search Report and Written Opinion for WO201617236.

Connon, et al., High-Throughput Methods for Microorganisms in Very Low-Nutrient Media Yield Diverse New Marine Isolates, Applied and Environmental Microbiology, Aug. 2002, p. 3878-3885.

Zengler, et al., Cultivating the uncultured. PNAS, 2002, vol. 99, No. 24, p. 15681-15686.

Stevenson, et al., New Strategies for Cultivation and Detection of Previously Uncultured Microbes, Applied and Environmental Microbiology, 2004, p. 4748-4755.

Laffert, et al., GigaMatrixTM: An Ultra High-Throughput Tool for Accessing Biodiversity, Journal of Association for Laboratory Automation, Aug. 2004, p. 200-208.

Ingham, et al., The micro-Petri dish, a million-well growth chip for the culture and high-throughput screening of microoganisms, PNAS, 2007, vol. 104, No. 46, p. 18217-18222.

Bollmann, et al., Incubation of Enviro Samples in a Diffusion Chamber Increases the Diversity of Recovered Isolates, Applied and Environment Microbiology, Oct. 2007, p. 6366-3690.

Miller, et al., "Basic Concepts of Microarrays and Potential Applications in Clinical Microbiology", Clinical Microbiology Reviews, Oct. 2009, p. 611-633.

Nichols, et al., Use of Ichip for High-Throughput In Silu Cullivation of "Uncultivable" Microbial Species, Applied and Environmental Microbiology, 2010, p. 2445-2450.

Vartoukian, et al., Strategies for culture of 'unculturable' bacteria, FEMS Microbiol Lett 2010, 309, p. 1-7.

Jung et al., Cell-free DNA in the blood as solid tumor biomarker—A Critical appraisal of the literature, Clinica Chimica Acta, 2010, 411, p. 1611-1624.

Lecomle, et al., Isolation and identification of soil bacteria growing at the expense of arbuscular mycorrhizal fungi, FEMS Microbiol Lett 2011, vol. 317, p. 43-51.

Stewart, Growing Unculturable Bacteria, Journal of Bacteriology, 2012, vol. 194 No. 16 p. 4151-4160.

Ma, et al., Gene-targeted microfluidic cultivation validated by isolation of a gut bacterium listed in Human Microbiome Project's Most Wanted taxa' PNAS, 2014, vol. 111, No. 27, p. 9768-9773.

Tandoga, et al., Isolation of Microorganisms Using Constrictions, PLOS ONE, 2014, vol. 9, No. 6, p. 1-7.

Chen, et al., High-throughput analysis and protein engineering using microcapillary arrays, Nature Chemical Biology, 2015 doi:10.1038/nchembio.1978.

* cited by examiner

APPARATUS AND METHOD FOR PICKING BIOLOGICAL SAMPLE

CROSS REFERENCE TO RELATED APPLICATIONS

This application is a continuation of U.S. Nonprovisional patent application Ser. No. 15/788,772 filed on Oct. 19, 2017, which claims the benefit of U.S. Provisional Patent Application No. 62/484,395 filed Apr. 12, 2017, and is a continuation-in-part of U.S. Nonprovisional patent application Ser. No. 15/135,377 filed on Apr. 21, 2016, which claims the benefit of U.S. Provisional Patent Application No. 62/299,088 filed Feb. 24, 2016, U.S. Provisional Patent Application No. 62/292,091 filed Feb. 5, 2016, and U.S. Provisional Patent Application No. 62/150,677 filed Apr. 21, 2015. The disclosure of each of these prior-field applications is incorporated herein in its entirety.

BACKGROUND

Microbial cells, such as bacteria, fungi, archaea, or viruses are often used as carriers in genomic research to replicate or express specific genes or proteins. Isolates of particular microbial species or variants are often isolated from mixed microbial populations. When grown in petri dishes, microbial cells usually form colonies. The microbial colonies can be hand-picked using a picker, such as a toothpick, and placed in individual wells of a microwell plate for subsequent incubation. Such hand-picking can be time consuming and tedious.

Automated systems for colony picking became available in recent years. In these systems, microbial colonies can be identified by computer vision technology, and a picker mounted on a robotic arm can be used to transfer material from selected colonies to destination microwell plates (such as 96-well or 384-well plates). However, as the size of the colonies may be quite large (in a range of millimeters, for example) and the colonies of interest may appear in unpredictable positions, these automated systems require analysis of the image of the culture media for detection of the right colony to pick from, which could involve complicated optical component as well as image analysis software. Further, the precision of the picking can be low.

SUMMARY OF INVENTION

In one aspect, the present invention provides a method of transferring a sample from at least one selected microwell of a microfabricated chip containing a plurality of microwells to a predetermined location in a destination sample holder using a picking instrument. The picking instrument comprises a picking pin, which has a distal tip, and has three degrees-of-freedom and configured to move in x, y, and z directions, the x, y directions constituting an x-y plane. The method includes: calibrating the position of the microfabricated chip relative to the position of the picking pin; determining the coordinates of the at least one selected microwell of the microfabricated chip for picking on the x-y plane relative to a position of the picking pin; based on a current position of the picking pin and the determined coordinates of the at least one selected microwell, moving the picking pin to a position above the location of the at least one selected microwell; dipping at least a portion of the distal tip of the picking pin into the at least one selected microwell to pick up a sample contained in the selected microwell; and moving the picking pin and transferring the sample to a predetermined location in the destination sample holder.

In some embodiments of the method, the calibration comprises: positioning the picking pin to a first position such that its distal tip is above a first reference microwell or a first fiducial mark, and recording the coordinates of the first position in a data memory; positioning the picking pin to a second position such that its distal tip is above a second reference microwell or a second fiducial mark, and recording the coordinates of the second position in the data memory; and calculating the coordinates of the at least one selected microwell based on the recorded coordinates of the first and second positions of the distal tip of the picking pin. Positioning the picking pin to the first and the second positions can be performed under surveillance of an image capture device and with aid of a digital display, where the image capture device provides images of the picking pin at the first and the second positions to the digital display.

In some embodiments, the calibration comprises calibrating the coordinates of one or more marks created by the picking pin during calibration. The calibration comprises: positioning the picking pin above the microfabricated device at provided (e.g., previously known or estimated) coordinates of the at least one target microwell of a microfabricated chip, lowering the picking pin such that the distal tip of the picking pin contacts the microfabricated device and creates at least one mark; retracting the picking pin; determining the displacement of the coordinates of the at least one mark from the provided coordinates of the at least one target microwell, (e.g., by examining the position of the at least one mark relative to the position of the at least one target microwell under a microscope); and calibrating the position of the microfabricated chip relative to the position of the picking pin based on the determined displacement. In such embodiments, the microfabricated chip used in the calibration can be the same microfabricated chip where the at least one selected microwell for picking is located, or a different microfabricated chip having the same specifications or different specifications.

In some embodiments of the method, the calibration comprises: (a) using an image capture device to capture one or more images of at least a portion of the microfabricated chip, and determining the coordinates of the at least one selected microwell based on an analysis of the one or more captured images; and (b) using an optical aligner to determine the coordinates of the position of the picking pin. In some of such embodiments, the optical aligner comprises a first light source, a first light detector, a second light source, and a second light detector, where the first light source and the first light detector are arranged such that a first light beam emitted from the first light source and received by the first light detector is along the y direction, and the second light source and the second light detector are arranged such a second light beam emitted from the second light source and received by the second light detector is along the x direction, and wherein using the optical aligner to determine the coordinates of the position of the picking pin comprises: translating the picking pin along the x direction and detecting the x coordinate of the picking pin when the first light beam along the y direction is blocked by the picking pin, x0; translating the picking pin along the y direction and detecting the y coordinate of the picking pin when the second light beam along the x direction is blocked by the picking pin, y0; and determining the coordinates of the position of the picking pin based on its offset in the x direction relative to x0, and its offset in the y direction relative to y0.

In alternative embodiments, instead of an optical aligner, a touchscreen is used to determine the coordinates of the location of the picking pin.

In some embodiments of the method, dipping the picking pin comprises inserting the distal tip of the picking pin into the at least one selected microwell such that the distal tip of the picking pin has traveled a predetermined distance into the microwell; and retracting the distal tip of the picking pin out of the at least one selected microwell.

In some embodiments of the method, dipping the picking pin comprises inserting the distal tip of the picking pin into the selected microwell; determining whether the distal tip of the picking pin has contacted the bottom of the selected microwell; and upon confirmation that the distal tip has contacted the bottom of the selected microwell, retracting the distal tip out of the at least one selected microwell. In some of these embodiments, determining whether distal tip of the picking pin has contacted the bottom of the selected microwell can be based on a distance in the z direction traveled by the picking pin.

In some embodiments of the method, the picking instrument further comprises a pressure sensor operably coupled with the picking pin for sensing an opposition force experienced by the picking pin when the distal tip of the picking pin contacts an object, and determining whether the distal tip of the picking pin has contacted the bottom of the at least one selected microwell is based on a detected opposition force when the distal tip of the picking pin contacts the bottom of the at least one selected well.

In some embodiments of the method, the at least one selected microwell includes an oil layer covering the sample, and dipping the picking pin comprises passing at least a portion of the distal tip of the picking pin through the oil layer.

In some embodiments of the method, the predetermined location in the destination sample holder is a well containing a culture media, and transferring the sample to the predetermined location in the destination sample holder comprises at least one of: (A) advancing and retracting the picking pin through at least a portion of the culture media repeatedly, and (B) dithering the distal tip of the picking laterally in the culture media.

In some embodiments of the method, after transferring the sample to a predetermined location in the destination sample holder, the picking pin is moved away from the destination sample holder and sterilized with a sterilization device.

In another aspect, the present invention provides a picking instrument, which includes a picking pin having a distal tip and three degrees-of-freedom and configured to move in x, y, and z directions, the x, y directions constituting an x-y plane; a loading platform comprising a first area and a second area, the first area configured to accommodate and secure a microfabricated chip including a plurality of microwells; and a computer operably connected to the picking pin, the computer having a data memory and a processor, and including a computer program product that enables the calibration of the coordinates of at least one selected microwell of the microfabricated chip on the x-y plane relative to a position of the picking pin, and enables the picking pin to: move to a position above the at least one selected microwell in the plurality of the microwells of the microfabricated chip; pick a sample contained in the selected microwell; move to a predetermined location at the destination sample holder; and transfer the picked sample to the predetermined location at the destination sample holder.

In some embodiments, the second area of the picking instrument is configured to secure a destination sample holder having a plurality of wells that have greater dimensions than the microwells of the microfabricated chip. In alternative embodiments, the second area is configured to secure another microfabricated chip having a plurality of microwells.

In some embodiments of the picking instrument, the movement of the picking pin is driven by three programmatically controlled motors, each motor configured to move the picking pin in the x, y, and z direction independently, respectively.

In some embodiments of the picking instrument, the picking pin is mounted on a spring.

In some embodiments of the picking instrument, a pressure sensor is coupled with the picking pin, where the pressure sensor is configured to sense an opposition force experienced by the picking pin when the distal tip of the picking pin contacts an object.

In some embodiments, the picking instrument further includes a camera configured to capture at least a portion of the microfabricated chip when it is loaded onto the loading platform. The camera can be in a fixed spaced relationship with the loading platform.

In some embodiments, the loading platform is movably mounted on a rail structure.

In some embodiments, the picking instrument further includes an optical aligner configured to determine the coordinates of the picking pin. In certain of these embodiments, the optical aligner can include a first light source, a first light detector, a second light source, and a second light detector, where the first light source and the first light detector are arranged such that a first light beam emitted from the first light source and received by the first light detector is along the y direction, and the second light source and the second light detector are arranged such a second light beam emitted from the second light source and received by the second light detector is along the x direction.

In some embodiments, the picking instrument further includes a sterilization device that is capable of sterilizing the distal tip of the picking pin.

In some embodiments, a method of operating a picking instrument as described herein is provided. The picking instrument includes a picking pin having a distal tip and three degrees-of-freedom and configured to move in x, y, and z directions, the x, y directions constituting an x-y plane; and a loading platform comprising a first area and a second area, the first area configured to accommodate and secure a microfabricated chip including a plurality of microwells, and the second area configured to accommodate and secure a destination sample holder. The picking pin is operably connected to a computer, the computer including a computer program product that enables the determination of the coordinates of at least one selected microwell of the microfabricated chip on the x-y plane relative to a position of the picking pin based on a calibration of the position of at least one mark on the microfabricated chip relative to a position of the picking pin. The first area of the loading platform is loaded with a first microfabricated chip having a top surface defining a plurality of microwells, and the second area of the loading platform is loaded with a destination sample holder. In the method, the position of the microfabricated chip is calibrated relative to a position of the picking pin using any of the methods described herein. The coordinates of the at least one selected microwell (for picking a sample) of the first microfabricated chip on the x-y plane relative to the position of the picking pin are determined based on the calibration. Based on the determined coordinates of the at least one selected microwell of the first microfabricated chip, the picking pin is moved to a position above the location of the at least one selected microwell of the first microfabricated chip. At least a portion of the distal tip of the picking pin is dipped into the at least one selected microwell of the first microfabricated chip to pick up a sample contained in the at least one selected microwell. The picking pin is moved to transfer the picked sample to a predetermined location in the destination sample holder.

In some embodiments, the above method further comprises: removing the first microfabricated chip from the first area of the loading platform; loading a second microfabricated chip into the first area of the loading platform; without performing further calibration, determining the coordinates of at least one selected microwell of the second microfabricated chip on the x-y plane relative to the position of the picking pin. The method can further include: based on the determined coordinates of the at least one selected microwell of the second microfabricated chip, moving the picking pin to a position above the location of the at least one selected microwell of the second microfabricated chip; dipping at least a portion of the distal tip of the picking pin into the at least one selected microwell of the second microfabricated chip to pick up a sample contained therein; and moving the picking pin to transfer the picked sample to a predetermined location in a same or different destination sample holder.

In any embodiments of the methods or picking instrument as described herein, the surface density of the plurality of microwells of the microfabricated device or chip can be at least 150 microwells per cm$^2$, at least 250 microwells per cm$^2$, at least 400 microwells per cm$^2$, at least 500 microwells per cm$^2$, at least 750 microwells per cm$^2$, at least 1,000 microwells per cm$^2$, at least 2,500 microwells per cm$^2$, at least 5,000 microwells per cm$^2$, at least 7,500 microwells per cm$^2$, at least 10,000 microwells per cm$^2$, at least 50,000 microwells per cm$^2$, at least 100,000 microwells per cm$^2$, or at least 160,000 per cm$^2$. Each microwell of the plurality of microwells of the microfabricated device or chip can have a diameter of from about 5 µm to about 500 µm, from about 10 µm to about 300 µm, or from about 20 µm to about 200 µm.

DETAILED DESCRIPTION

In one aspect of the present disclosure, an apparatus (or picking instrument) is provided for transferring a sample from a selected microwell on a microfabricated device or chip to a predetermined location in a destination (or target) sample holder. In another aspect of the present disclosure, a method using the picking instrument to transfer a sample from a selected microwell on a microchip is provided. In the following, the apparatus and the method will be described in conjunction with each other.

Figure 1:
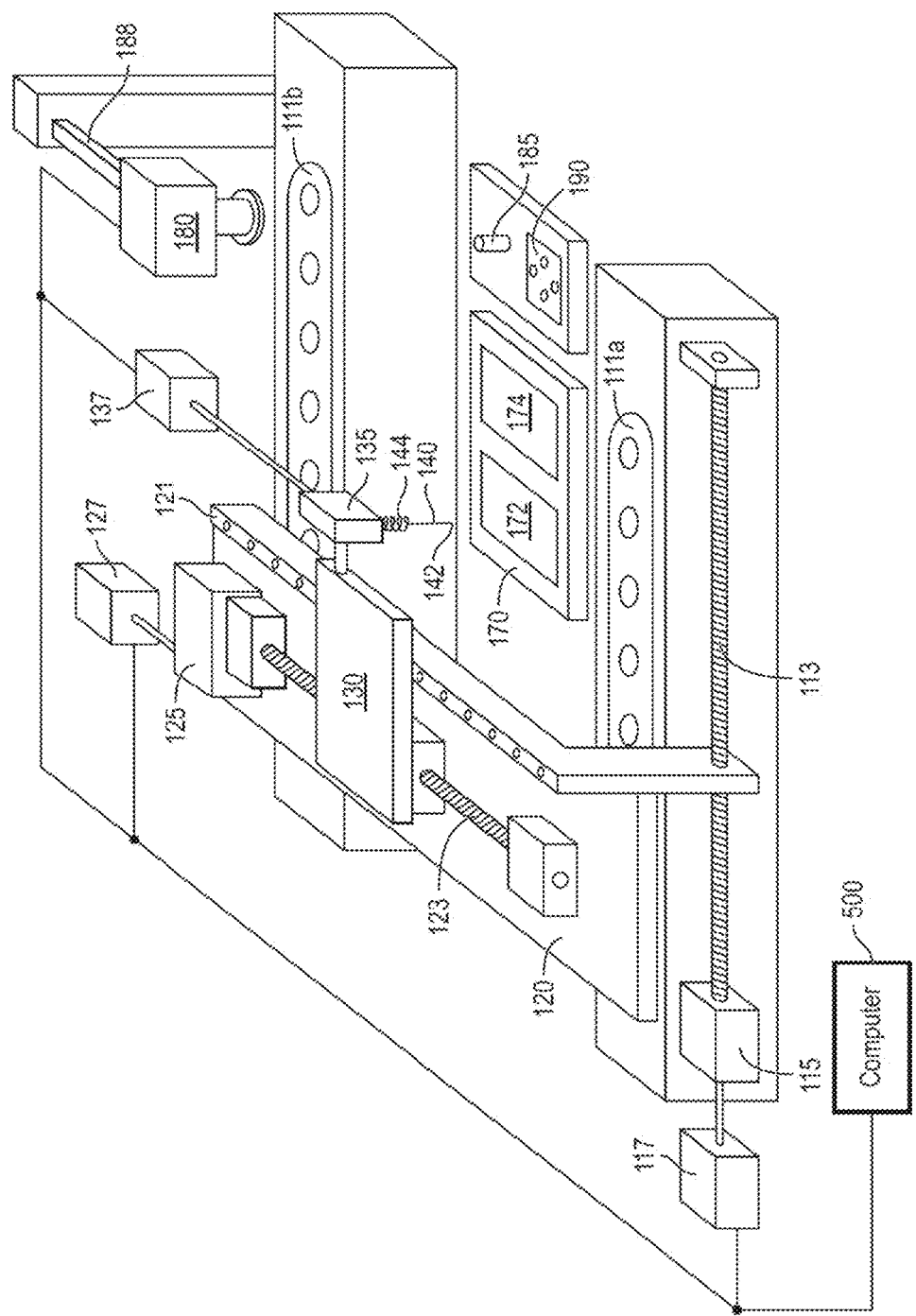
FIG. 1 is a schematic diagram for an example picking instrument in accordance with embodiments of the present invention.

As illustrated in FIG. 1, the picking instrument 100 includes a pair of rails 111a and 111b (x-rails) extending in an x-direction, and a block 120 that can slide along the x-rails in the x-direction. Block 120 includes a y-rail 121 extending in a direction perpendicular to the rails 101 and 102. Y-rail 121 includes a bottom part that is rotatably coupled with a screw 113 which is installed on a side of the rail 101 and in the x direction. Screw 113 is driven (rotated) by x-motor 115, which receives control signals from the x-controller 117. The rotation of screw 113 moves the y-rail 121 (and block 120 as a whole) along the x-direction.

A screw 123 extending along the y-rail is installed on block 120. Screw 123 is driven (rotated) by y-motor 125, which receives control signals from the y-controller 127. Block 130 is rotatably coupled with screw 123, the rotation of which moves the block 130 along the y-direction which is perpendicular to the x-direction.

A z-motor 135 is connected with block 130. A picking pin 140, which has a distal tip (or distal end) 142, is mounted on z-motor 135, which drives the picking pin 140 in the z-direction (which is perpendicular to both the x- and y-direction). The proximal end of the picking pin 140 is coupled with z-motor 135 via a spring 144. Although only one picking pin is shown, it is understood that a plurality of picking pins (e.g., mounted in a fixed spaced relationship with each other) are also contemplated. For certain applications described herein, the range of movement of the picking pin 140 on the z-axis is typically much smaller compared to the distance it travels along the x- or y-direction. Thus, in an implementation, the picking pin 140 can be directly coupled with z-motor 135 (e.g., with an internal screw coupling mechanism in the z-motor 135) and not through an externally mounted screw coupling. Each of the motor controllers 117, 127, and 137 are operably connected to a computer 500 for receiving control signals as well as providing feedback on the position information about the respective motors.

Also as illustrated in FIG. 1, the picking instrument 100 includes a loading platform 170. The loading platform can be a fixed immobile platform, or movable on a rail structure to facilitate loading and unloading of one or more sample holders. The platform 170 includes a first area (or source area) 172 and a second area (or destination area) 174. The first area 172 is configured to accommodate and secure a microfabricated chip including a plurality of microwells. The second area (destination area) 174 may be configured to accommodate and secure a similar microfabricated chip, or a sample holder having a plurality of wells that have greater dimensions than the microwells of the microfabricated chip. For example, the target sample holder can be a commercially available 96-well plate or 384-well plate, where the diameters of the wells in such a holder can range from about 3 mm to about 7 mm, and a depth of about a few millimeters to tens of millimeters, e.g., about 6 mm to about 30 mm (or greater).

Figure 2:
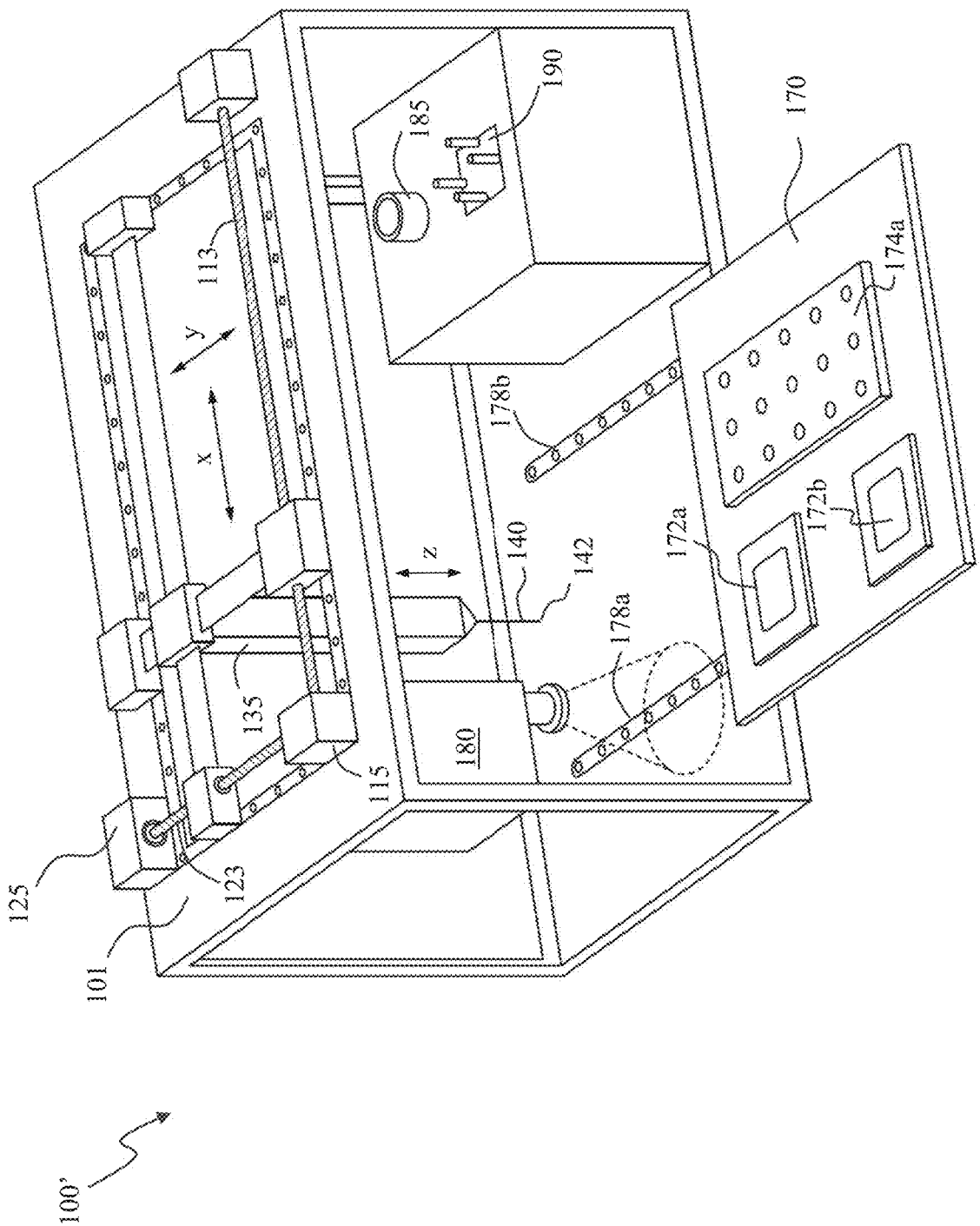
FIG. 2 is a schematic diagram for another example picking instrument in accordance with embodiments of the present invention.

FIG. 2 depicts an example picking instrument 100' of the present invention where certain components are arranged differently from FIG. 1. Same reference numerals are used in FIG. 2 to denote those elements having same or similar functions. The controllers, control lines and computer are not explicitly shown in FIG. 2. The picking instrument 100' as depicted in FIG. 2 has a box-like overall structure with a skeletal frame 101. The picking pin 140 having a distal tip 142 is mounted on z-motor 135, which drives the picking pin 140 along the z direction, whereas the x, y direction motion of the picking pin is independently driven by the x-motor 115 along x-screw 113 and y-motor 125 along y-screw 123, respectively. In the picking instrument 100' illustrated in FIG. 2, the loading platform 170 is movable on a rail structure including two rails 178a and 178b. Picking operations can be suspended when the loading platform 170 is drawn out to load or unload sample holders, and can resume when the loading platform 170 is pushed back into the box and locked at a preset location. As shown in FIG. 2, the loading platform 170 is installed with a first microfabricated chip 172a, a second microfabricated chip 174b, and a microplate 174a. Either the first microfabricated chip 172a or the second microfabricated chip 172b can be used as the source for the picking pin to pick from, or as the destination for the picking pin to deposit the picked material. The microplate 174a can be used as a target sample holder to receive the picked material deposited by the picking pin. The camera 180 is fixedly installed on the skeletal frame 101 of the picking instrument 100'.

Figure 3:
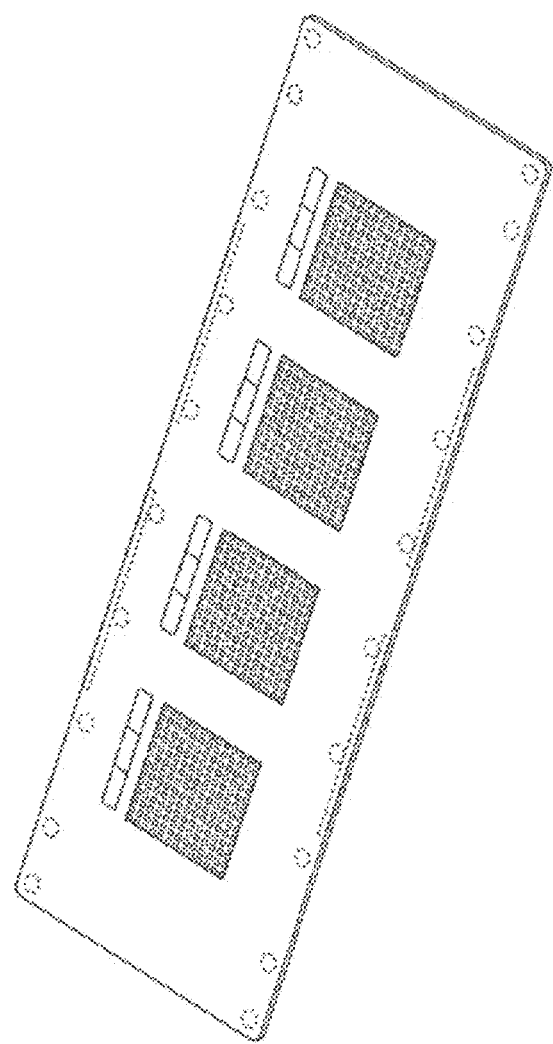
FIG. 3 is a schematic depiction of an example microfabricated chip having an array of microwells in accordance with embodiments of the present invention.

As used herein, a microfabricated device or chip may define a high density array of microwells (or experimental units). For example, a microfabricated chip comprising a "high density" of microwells may include about 150 microwells per $cm^2$ to about 160,000 microwells or more per $cm^2$ (for example, at least 150 microwells per $cm^2$, at least 250 microwells per $cm^2$, at least 400 microwells per $cm^2$, at least 500 microwells per $cm^2$, at least 750 microwells per $cm^2$, at least 1,000 microwells per $cm^2$, at least 2,500 microwells per $cm^2$, at least 5,000 microwells per $cm^2$, at least 7,500 microwells per $cm^2$, at least 10,000 microwells per $cm^2$, at least 50,000 microwells per $cm^2$, at least 100,000 microwells per $cm^2$, or at least 160,000 microwells per $cm^2$). A substrate of a microfabricated chip may include about or more than 10,000,000 microwells or locations. For example, an array of microwells may include at least 96 locations, at least 1,000 locations, at least 5,000 locations, at least 10,000 locations, at least 50,000 locations, at least 100,000 locations, at least 500,000 locations, at least 1,000,000 locations, at least 5,000,000 locations, or at least 10,000,000 locations. The arrays of microwells may form grid patterns, and be grouped into separate areas or sections. The dimensions of a microwell may range from nanoscopic (e.g., a diameter from about 1 to about 100 nanometers) to microscopic. For example, each microwell may have a diameter of about 1 μm to about 800 μm, a diameter of about 25 μm to about 500 μm, or a diameter of about 30 μm to about 100 μm. A microwell may have a diameter of about or less than 1 μm, about or less than 5 μm, about or less than 10 μm, about or less than 25 μm, about or less than 50 μm, about or less than 100 μm, about or less than 200 μm, about or less than 300 μm, about or less than 400 μm, about or less than 500 μm, about or less than 600 μm, about or less than 700 μm, or about or less than 800 μm. In exemplary embodiments, the diameter of the microwells can be about 100 μm or smaller, or 50 μm or smaller. A microwell may have a depth of about 25 μm to about 100 μm, e.g., about 1 μm, about 5 μm, about 10 μm, about 25 μm, about 50 μm, about 100 μm. It can also have greater depth, e.g., about 200 μm, about 300 μm, about 400 μm, about 500 μm. The microfabricated chip can have two major surfaces: a top surface and a bottom surface, where the microwells have openings at the top surface. Each microwell of the microwells may have an opening or cross section having any shape, e.g., round, hexagonal, or square. Each microwell may include sidewalls. For microwells that are not round in their openings or cross sections, the diameter of the microwells described herein refer to the effective diameter of a circular shape having an equivalent area. For example, for a square shaped microwell having side lengths of 10×10 microns, a circle having an equivalent area (100 square microns) has a diameter of 11.3 microns. Each microwell may include a sidewall or sidewalls. The sidewalls may have a cross-sectional profile that is straight, oblique, and/or curved. Each microwell includes a bottom which can be flat, round, or of other shapes. The microfabricated chip (with the microwells thereon) may be manufactured from a polymer, e.g., a cyclic olefin polymer, via precision injection molding or some other process such as embossing. The chip may have a substantially planar major surface. FIG. 3 shows a schematic depiction of a microfabricated chip, whose edges are generally parallel to the directions of the rows and the columns of the microwells on the chip.

The high density microwells on the microfabricated chip can be used to conduct various experiments, such as growth or cultivation or screening of various species of bacteria and other microorganisms (or microbes) such as aerobic, anaerobic, and/or facultative aerobic microorganisms. The microwells may be used to conduct experiments with eukaryotic cells such as mammalian cells. Also, the microwells can be used to conduct various genomic or proteomic experiments, and may contain cell products or components, or other biological substances or entities, such as a cell surface (e.g., a cell membrane or wall), a metabolite, a vitamin, a hormone, a neurotransmitter, an antibody, an amino acid, an enzyme, a protein, a saccharide, ATP, a lipid, a nucleoside, a nucleotide, a nucleic acid (e.g., DNA or RNA), etc. Thus, a sample picked from a microwell can include any one or mixture of the above microorganisms, eukaryotic cells, biological entities or substances, depending on the experiments being conducted in such a microwell.

As seen from the schematics shown in FIGS. 1 and 2 and the description herein, the picking pin 140 overall has three degrees-of-freedom and is configured to move in x, y, and z directions independently (x, y, and z directions are orthogonal to each other). Preferably, when the picking instrument is installed in place, the z direction is along the direction of gravity. The x, y directions constitute an x-y plane. As the picking pin predominantly travels along the x-y plane, the coordinates of the microwells, fiducial marks, or other marks of the microfabricated chip are herein used as a shorthand to refer to the x, y coordinates of these objects in the x-y plane.

The picking pin 140 may be made from a metal or an alloy. Although it is depicted as having a constant-diameter elongated needle-like shape extending along the z-axis, the pin can include a section or sections having other shapes and/or orientations, e.g., a curved or serpentine shape. The distal tip of the pin can also have various shapes and configurations. For example, it can have a cone shape with a pointed end, a flat end, a round end, or an obliquely cut end, etc. If the microwells of interest are covered by a layer of membrane, the distal tip of the picking pin can be constructed and configured such that it can pierce through such membrane. The pin can have a hollow interior, in which case it can be connected with an aspiration device or pump at its back end to pick a sample up with the aid of vacuum (and the release of the sample can be aided by blowing air, much like a micropipette). The bottom surface and/or the side surface of the distal tip of the picking pin may include patterns, such as depressions, cuts, embossing or protrusions, for increased friction which can be beneficial for retaining the sample during picking. The distal tip of the picking pin may further include a material, or treated and/or coated with a surface chemistry modifier for surface characteristics that favor attachment of microbial cells or other substances of interest. The diameter of the stem portion of the picking pin 140 (or its greatest cross section dimension) can be about 100 microns to a few millimeters, depending on the material and construction of the pin, and the diameter of the distal tip portion may be smaller than the diameter of the microwells of the microfabricated chip. Through the motors and their associated controllers, which are in turn controlled by command signals received from the computer 500 (and generated by the control computer program product), the picking pin is programmatically controlled to move to a position above a selected microwell in the microwells of the microfabricated chip, pick a sample contained in the selected microwell, move to a predetermined location at the target sample holder, and transfer or deposit at least a portion of the picked sample to the predetermined location at the target sample holder. As will be further described below, most of the operations of the picking instrument, such as the actuation of the motors and movement of the picking pin, can be ultimately controlled by a computer via appropriate computer program product (or computer software), such control can be effectuated by use of appropriate adaptors, controllers, and other interface elements that can convert and transmit data between the computer and various peripheral devices, as known to an ordinarily skilled in the art. The computer also provides a user interface for a user to enter information, e.g., identification of the selected microwell(s) on the chip, and performs the necessary data storage, calculation, image processing, and other functions as described herein relevant to the operations of the picking instrument.

In the example system depicted in FIGS. 1 and 2, the movement of the picking pin is driven by three programmatically controlled motors, each motor configured to move the picking pin in the x, y, and z direction independently, respectively. The operations of the picking instrument and picking pin are further described below.

Figure 4:
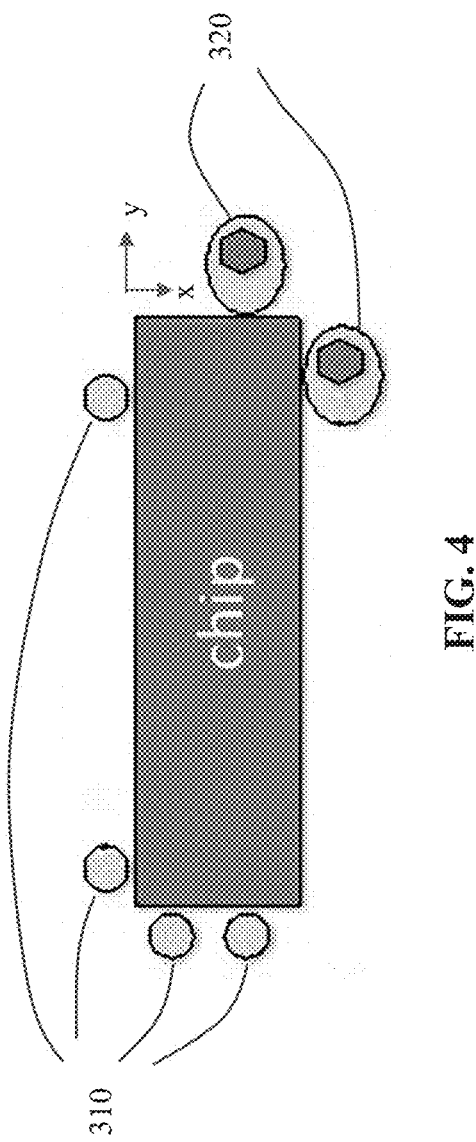
FIG. 4 is a schematic top view of a mechanism for securing an example microfabricated chip in accordance with embodiments of the present invention.

A microfabricated chip as described herein is loaded on the first area 172 of the loading platform 170. Preferably, the chip is loaded with its major planar surface parallel with the x-y plane of the picking instrument. As illustrated in FIG. 4, which is a schematic top view of an example mechanism for securing the microfabricated chip, the chip is secured by a number of locating pins 310 on the platform (shown on the left and top sides of the chip) and two screws 320 on the opposing sides with associated elliptical caps, the tightening of which pushes the chip against the locating pins, thereby providing the clamping force to secure the chip in place. When the chip has a rectangular ship and its rows/columns of microwells are running parallel to the side edges of the chip, the chip is preferably loaded such that its side edges are along the x and y direction of the picking pin, as illustrated in FIG. 4.

The destination sample holder may be secured on the second area 174 using a similar mechanism as shown in FIG. 4. If the destination sample holder is a commercial 96-well or 384-well plate, the securing mechanism can be any commonly known techniques in the art, depending on the particular configuration of the sample holder. The type of the sample holder and its dimensions and other configuration parameters can be stored in a data memory of the computer 500 for computing the coordinates of the destination wells into which the picked material is to be released or deposited.

In some embodiments, before loading the chip onto the picking instrument, desired experiments have been performed in the microwells, and the resulting microwells have been examined, e.g., under a microscope, to select one or more particular microwells that may contain a sample of interest for picking (e.g., for further growth, analysis and experiments). Such determination may be by color or other appearance characteristics of the contents in the microwells, and could be aided by fluorescence or phosphorescence emission. As the microwells may be arranged in highly regular patterns, such as arrays or matrices, the selection can be based on the row and column number of a selected microwell, or other geometrical parameters corresponding to the pattern of the microwells on the chip. In alternative embodiments, the determination and selection can be made after the chip is loaded onto the picking instrument, where an on-board camera (installed on the picking instrument) can be used to examine the chip to make the selection. Information about such selected microwell(s) can be saved in the data memory of the computer (e.g., using a graphic user interface on the computer) for subsequent use, as further explained below.

In some embodiments, when working with a microfabricated chip having densely packed microwells having extremely small sizes (e.g., diameters about 100 µm or smaller), the movement of the picking pin on the x-y plane needs to be particularly precise. The x- and y-motors can be selected to be accurate and reproducible down to the micron level. However, there may be slight variations in the loading position and/or orientation of each newly loaded microfabricated chip, the picking pin may deform slightly after repeated use, and the motor positions may gradually drift over time. Thus, it is important to precisely determine or calibrate the x- and y-positions of the microwells relative to that of the picking pin to address such loss of precision over time or usage. Such calibration ensures that the correct microwell is picked. When many picking operations (or picking cycles) are needed from a same chip, calibration can also be performed in between operations.

When a specific microfabricated chip is loaded onto the picking instrument, since the manufacture specifications or configuration parameters of the microfabricated chip (e.g., dimensions of the microwells, spacing between the microwells, number of rows and columns of the microwells, grid pattern of the microwells, distance of reference microwells from the edges or sides of the chip) are known, the corresponding data can be loaded or saved in the data memory of the computer, and can be used for calibration purpose.

In some embodiments, the calibration can be performed by aligning the distal tip of the picking pin on the z-direction directly with a few reference microwells or fiducial marks of the microfabricated chip. For example, the picking pin can be first positioned at a first position such that its distal tip is above a first reference microwell. The coordinates of this first position can be saved in the data memory (e.g., entered by a user via a graphical user interface on a display of the computer). Then, the picking pin is moved to a second position such that its distal tip is above a second reference microwell (different from the first reference microwell). The coordinates of this second position can also be saved in the data memory. One or both of the first and the second reference microcells used in this process can be the selected microwell(s) that have been determined to contain sample of interest, or they can be any other microwells on the chip. For broader applicability, the first reference microwell and the second reference microwell can be well spaced on the chip. For example, the first reference microwell may be located on the upper left corner of the chip, and the second reference microwell may be located on the bottom right corner of the chip. Based on the saved coordinates of the first position and the second position, the coordinates of the selected microwell(s) can be computed by the computer utilizing the information about the pattern of the microwells of the chip. Indeed, based on the pattern of the wells, this procedure may be used to compute the positions of all microwells on the chip.

Positioning or aligning the picking pin at the first and the second positions can be performed under surveillance of an image capture device (e.g., a camera or a microscope) and with aid of a digital display, where the image capture device serves as the source of the images of the picking pin at the first and the second positions shown in the digital display. The image capture device may be mounted at an angle with respect to the z-direction to view both the distal tip of the picking pin and the reference well. To reduce uncertainty of the z-direction alignment along the line of sight, the image capture device can be moved around to a few different positions to view the positioning of the pin relative to the reference well from different perspectives, and the pin position may be adjusted by a user for improved alignment. The above mentioned first reference microwell and/or second reference microwell can also be replaced by a fiducial mark (or fiducial marks) on the chip. As the positioning of the fiducial marks relative to the microwells are known for a given loaded microfabricated chip, in such a case, the positions of the selected microwells (or all microwells, if desired) can be computed by the first and/or second pin positions when the pin is aligned with the fiducial mark(s) and the manufacture specification parameters of the microfabricated chip.

In some embodiments, alignment of the picking pin with a third reference microwell or fiducial mark may be used for further improving the accuracy of the calibration. For example, suppose the microwell pattern of the chip is 500 rows×1000 columns grid pattern. The first reference microwell can be the first microwell of the first row (or of first column), the second reference microwell can be the $500^{th}$ row of the first column, and the third reference microwell can be the $500^{th}$ row of the $1000^{th}$ column. Such a triangular selection of reference microwells may help correct any orientation misalignment of the side edges of the chip.

In some embodiments, the calibration can be performed by locating the microwells on the microfabricated chip and the picking pin separately without performing direct alignment of the pin against any microwells (or fiducial marks) of the chip. This can be done in the following manner. An image capture device is used to take one or more images of a loaded microfabricated chip (or a portion thereof). The image capture device, e.g., a camera, can be an integral part of the picking instrument. For example, and as illustrated in FIG. 1, a camera 180 can be mounted on a support arm 188 and positioned with a preset distance and angle with respect to the loading platform 170. The camera can be programmed to take one or more images (e.g., one or more top views of the loaded microfabricated chip or a portion thereof, with or without a portion of the platform or other immobile part of the picking instrument), and send the image(s) to computer 500. The computer performs image processing and recognition on the image(s) and determines the coordinates of the selected microwells (or all the microwells on the chip) in the instrument space. This can be based on the image recognition of the microwells themselves, or based on image recognition of certain fiducial mark(s) on the microfabricated chip distinct from the wells (e.g., certain marks that are located away from the wells, such as near the edges of the chip). As the camera 180 is in a known configuration with respect to the loading platform 170, the dimension and positions of the microwells or fiducial marks identified on the images can be directly correlated and converted to physical positions in the instrument or system space. In this manner, the exact physical locations or coordinates of the selected microwells or all of the microwells of the chip can be determined. The camera 180 illustrated in FIG. 2, installed in a slightly different manner than that in FIG. 1, can be used to in a similar fashion as described above (the computer and control line connecting the camera and the computer are not shown).

Figure 5:
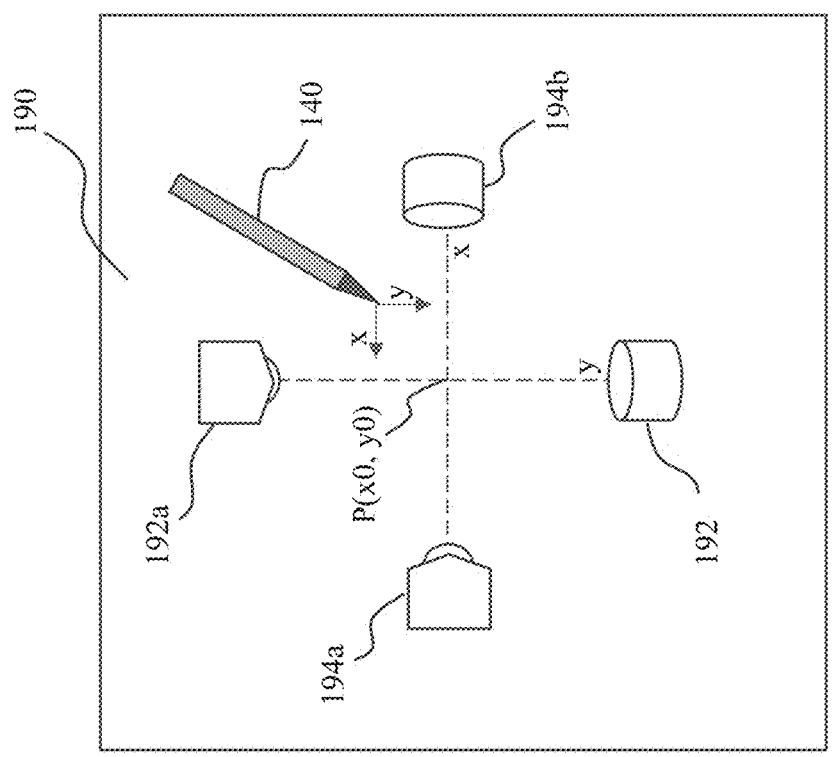
FIG. 5 is a schematic top view of an aligner for locating the position of the picking pin of an example picking instrument in accordance with embodiments of the present invention.

In addition to locating the position(s) of the selected microwell(s), the position of the picking pin is also located. This can be accomplished using an optical aligner (as shown in FIGS. 1, 2, and 5). FIG. 5 illustrates an implementation of such an aligner. Aligner 190 includes a light source 192a (e.g., a laser or LED) which shines a light beam onto a light detector 192b, and a light source 194a which shines a light beam onto a light detector 194b. The light source 192a and the detector 192b are arranged such that the optical axis of the light beam emitting from light source 192a and detected by detector 192b is along the y-direction. The light source 194a and the detector 194b are arranged such that the optical axis of the light beam emitting from light source 194a and detected by detector 194b is along the x-direction. To locate a current x and y position of the picking pin, the distal tip of the pin is moved between these two pairs of light sources and detectors (192a, 192b) and (194a, 194b) to disrupt these two light beams. As the positions of the light source 192a, detector 192b, light source 194a, detector 194b are fixed and known (and relevant data can be saved in the computer memory), the x-coordinate where the picking pin would block the x-beam, as well as the y-coordinate where the picking pin would block the y-beam, are both known, and hereinafter referred to as x0, y0, respectively. The position marked by (x0, y0) is also where the two light beams interest, and is shown as P(x0,y0) in FIG. 5.

The optical aligner 190 as shown in FIGS. 1, 2 and 5 can be operated as follows to locate the picking pin. Briefly, to precisely locate the picking pin on the x-direction, the picking pin 140 can be first positioned at an initial location near the aligner 190 (which can be accomplished by a user entering commands or parameters on a user interface to effect the movement of the pin to an initial location near the aligner, or by moving the pin automatically to the initial location using movement parameters pre-specified in the computer program), then the pin is translated on the x direction slowly between the light source 192a and detector 192b. The intensity of light detected on the detector 192b is monitored or recorded as a function of the x-motor position (which is tracked by the x-motor controller and fed to the computer). When the detected light on detector 192b reaches a minimum, the corresponding x-motor position is a reference x-motor position for which the x-coordinate of the picking pin is x0. As any x-motor position relative to this reference x-motor position can be tracked precisely by the x-controller, any current position of the picking pin in the x-direction can thus be determined based on the location of x0 and the corresponding x-motor position relative to the reference x-motor position (the difference between any x-motor position and the reference x-motor position can be readily converted to a physical distance based on a conversion factor specific to the x-motor). Similarly, to calibrate the location of the picking pin 140 in the y-direction, the pin is translated on the y direction slowly between the light source 194a and detector 194b, and the intensity of light detected on the detector 194b is monitored to determine when the y-coordinate of the pin coincides with y0. As the picking pin position along the y-direction relative to y0 can be tracked precisely by the y-controller, any current position of the picking pin in the y-direction can thus be determined.

In another embodiment, a touchscreen or touchpad that is sensitive to pressure, instead of an optical aligner, can be used as an aligner to locate the (x,y) coordinates of the pin. For example, the touchscreen can be installed in the area where the optical aligner (190 in FIG. 1) is installed. The touchscreen can have enough resolution to accurately locate the pin in space. For example, a touchscreen having a resolution of 4096 DPI which converts to approximately 6 microns per pixel, can be used. To use the touchscreen, the picking pin can be moved to a location in the x,y-plane above the touchscreen with a known motor position from optical encoders associated with the motors. The pin can then be lowered in the z-direction until it makes contact with the touchscreen. The touch signal generated by the touchscreen can be transferred to the computer to compute where the pin is located in space, and associate it with the motor positions.

Upon the completion of the above two steps (the order of the steps are of no significance), i.e., (1) locating the selected microwell(s) on the microfabricated chip using the image capture device and (2) locating the picking pin, e.g., using the aligner or the digital touch screen, the x- and y-travel distance needed by the pin to move from its current position to the selected microwell(s) can be calculated, based on which the pin can be translated to the selected microwell(s) to pick a sample.

The pin location on the z-direction may also be calibrated prior to picking operations. However, for many applications the pin travel on the z-direction does not need to be as precisely controlled as on the x- and y-direction. For example, before picking, the distal tip of the picking pin can be brought into contact (e.g., using a visual aid such as a microscope or camera) with the horizontal upper surface of a loaded microfabricated chip. This z-position can be used as a reference to set the extra predetermined distance for the pin to travel down the z-direction to pick a sample from a microwell based on the depth of the microwells. For example, the predetermined distance can be set such that the distal tip of the picking pin is within a threshold distance from the bottom of the microwell, or it can be set such that the distal tip of the picking pin will touch the bottom of the microwell. If the pin is equipped with a pressure sensor (as further described below), such contact with the bottom of the microwell can be determined automatically by computer, in which case the calibration based on distance traveled can be omitted.

If the destination sample holder is also a microfabricated chip having a high density array of microwells, the coordinates of the predetermined location where the picked sample is to be deposited in the destination sample holder can be calibrated in a similar manner as described above.

After the calibration is performed, based on the calibrated coordinates of the selected microwell, the picking pin is moved to a position above the location of the selected microwell. Then the picking pin is inserted into and then withdrawn from the selected microwell to pick up a sample contained in the selected microwell. The sample may be adhered to the picking pin. In the dipping process, the picking pin can be lowered into the selected microwell for a predetermined distance based on the initial z position of the tip of the picking pin and the depth of the selected microwell. Such a distance should be sufficient to ensure that the picking pin contact the sample contained in the selected microwell. In some embodiments, it is desirable that the distal tip of the picking pin travels beyond (and slightly indenting) the bottom of the microwell. This may be beneficial because of chip nonuniformity or securing the chip slightly away from flat, and the extra distance the pin travels can help make up for these irregularities. The pin mount with the spring can allow some pushback from the bottoms of the microwells without damaging it or losing its registry with the motors. In such embodiments, during the dipping process, it is determined whether the distal tip of the picking pin has contacted the bottom of the selected microwell (based on the z-distance it has traveled), and upon confirmation that the distal tip has contacted the bottom of the selected microwell, the picking pin is retracted out of the microwell. Ensuring that the picking pin touches the bottom of the selected microwell can be through setting a z-travel distance of the picking pin from the mouth of the microwell downward to be slightly exceeding the nominal depth of the microwell (based on manufacture specifications).

In further embodiments, a pressure sensor (not shown) can be mounted at the proximal end of the picking pin (e.g., on the spring 144) for sensing an opposition force experienced by the picking pin when the distal tip of the picking pin contacts an object, e.g., the bottom of the selected microwell. Here, determining whether the distal tip of the picking pin has contacted the bottom of the selected microwell can be based on a detected opposition force when the distal tip of the picking pin contacts the bottom of the selected well. If the detected opposition force is greater than a preset threshold, it can be deemed that the contact has taken place. The pressure sensor can be coupled with an appropriate adaptor which can convert the detected force into digital signals to be fed to the computer running the computer program for the operation of the instrument.

After retracting the picking pin out of the selected microwell of the microfabricated chip, the picking pin is then moved to a position where the distal tip of the picking pin is over the predetermined location of the destination sample holder. This location can be a well of the sample holder. The well may include culture media or other substances for further tests on the picked sample. In such cases, the picking pin can then be dipped into the media, allowing the sample attached to the picking pin to be released and deposited in the media. The travel in the x-y plane from the selected microwell to the release site as well as the travel in the z-direction of the picking pin can be likewise controlled by the computer based on the coordinates of the destination location relative to the coordinates of the selected microwell of the microfabricated chip as well as the height of the destination sample holder, the depth of the well of the destination sample holder, and the filled level of the media in the well of the destination sample holder, etc.

In some embodiments, the calibration process as previously described can also be conducted by performing one or more "test picks" on a microfabricated chip (without needing to deposit any picked material to any destination location). To do this, one or more target microwells can be provided to the picking pin to test pick based on provided coordinates (e.g., previously known or estimated coordinates) of the target microwells. This can be done by, for example, inputting the relative position of the target microwells in the grid pattern, or physical coordinates. Then, similar to actual picking, the picking pin is moved to a position according to the provided coordinates of the target microwell(s), and the picking pin is lowered such that the distal tip of the picking pin contacts the microfabricated device and creates a mark (a physical dent). The picking pin is then retracted. The microfabricated chip can be taken out (or the loading platform is drawn out of the picking instrument box, as shown in FIG. 2) and the mark(s) are observed under a microscope that has sufficient magnification and measuring capabilities to accurately determine the displacement of the mark(s) made by the picking pin from the target or intended microwell. Based on the determined displacement, the position of the microfabricated chip as a whole, and any features of the chip, e.g., any microwells, fiducial marks, etc., relative to the position of the picking pin can be determined. Thereafter, in an actual picking operation, the position in the x,y plane of the picking pin is adjusted by this displacement so that the pin can be accurately moved to the selected microwell(s) for picking.

Figure 6:
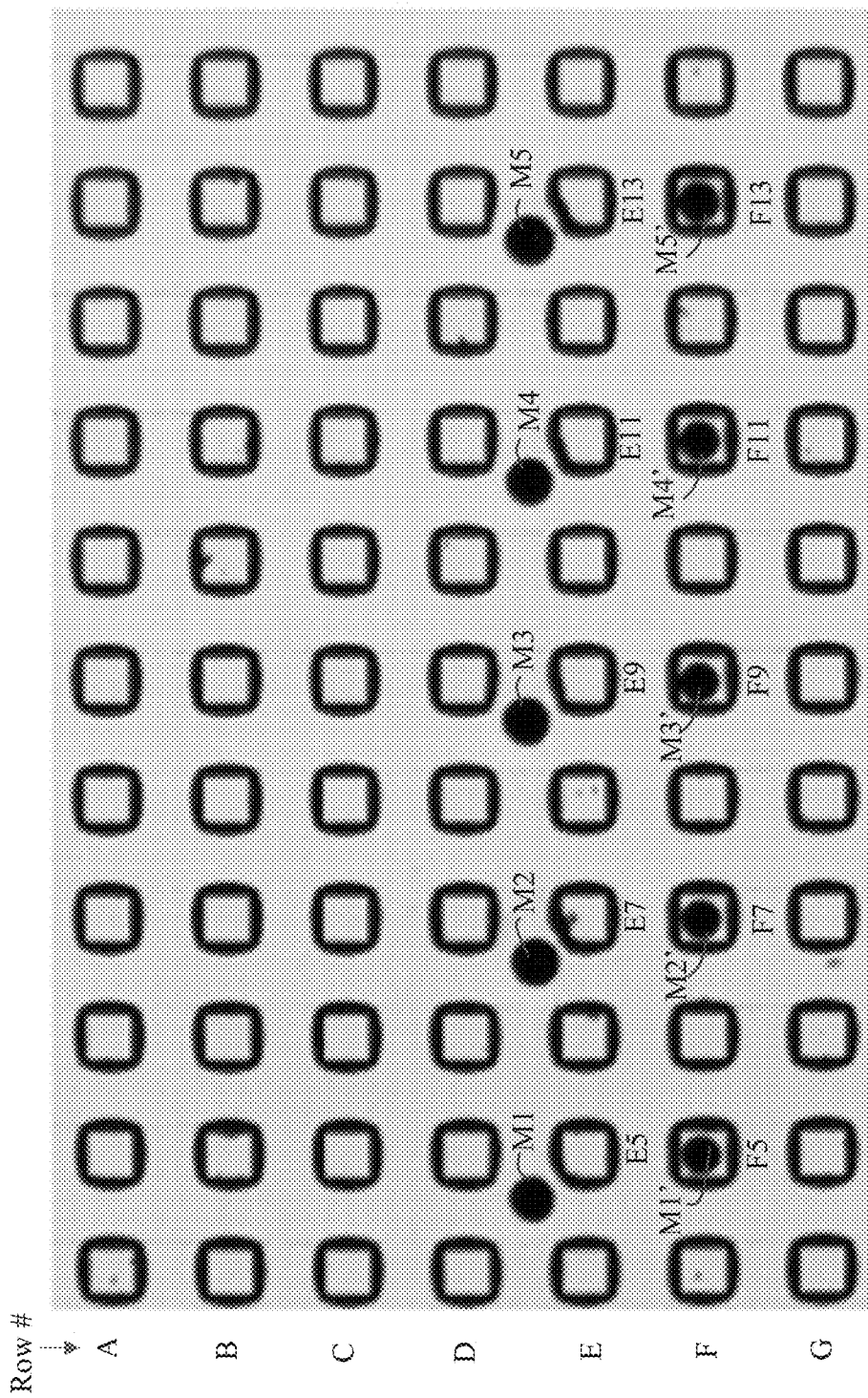
FIG. 6 is an image of an area of a microfabricated chip comprising a number of microwells and a number of marks created by a picking pin, in accordance with embodiments of the present invention.

As an illustration of this calibration method, FIG. 6 shows a portion of a grid pattern of microwells on a top surface of a microfabricated chip containing some marks made by the picking pin during a calibration run, observed under a microscope. The target microwells are E5, E7, E9, E11, and E13 (on the grid pattern). The picking pin made a series of marks M1, M2, M3, M4 and M5 based on assumed coordinates of the corresponding target microwells (these coordinates may be previously known by instrument specifications, or prior calibrations, etc.). Based on the displacement (in both x and y direction) of the positions of these marks made during the calibration relative to the corresponding intended or targeted microwells as observed under the microscope, an offset can be determined and saved to a data memory of the computer as described herein. Thereafter, in an actual picking run, the offset can be used to compensate or adjust the coordinates of the picking pin to accurately locate the selected microwells for picking. If the displacement is very small, it is possible that during this calibration, the picking pin contacts the bottom of target microwells, and make marks right in the target microwells. The extent/depth of the dents or marks made by the picking pin can be controlled by adjusting parameters relating to the pressure sensor loaded on the back of the picking pin.

To confirm the result of the calibration, another run of "test picks" was performed on the same microfabricated chip. This time, the target microwells specified were F5, F7, F9, F11, and F13. The offset determined in the previous calibration run was used to adjust the coordinates of the picking pin. As seen in FIG. 6, the marks made by the picking pin M1', M2', M3', M4', M5' in this run were located within the corresponding intended microwells, indicating the calibration was successful.

The microfabricated chip used in this calibration can be the same microfabricated chip where subsequent picking operations are performed, or a different microfabricated chip. In the latter scenario, after the calibration is done, the microfabricated chip is removed, and the microfabricated chip with microwells containing sample to be picked is installed. Due to the high manufacturing precision of the microfabricated chip as well as the precise positioning of the loading platform, installing a new microfabricated chip would not produce significant errors in positioning. Therefore, this calibration can be performed once on a microfabricated chip to be used for many other chips. These microfabricated chips can have same or different specifications, as long as the key parameters of the grid patterns are fed to the computer (e.g., the grid pattern itself, the center-to-center distance from two neighboring microwells, the positioning of the microwell of the first column and first row relative to the top and left edge of the microfabricated chip, etc.) at the beginning of the picking run, then the appropriate parameters for picking can be computed and adjusted automatically by the computer, without having to go through a similar calibration process.

When one needs to pick samples from more than one microwell from the microfabricated chip to a destination sample holder, after depositing the picked sample to the destination sample holder, the picking pin needs to be cleaned and/or sterilized to avoid cross contamination of the sample to be picked next from the material picked previously. The picking pin can be moved to a specific area where such sterilization is provided. As illustrated in FIGS. 1 and 2, sterilization can be performed via a sterilization device 185 (e.g., a heating coil into which the picking pin can be briefly dropped into where it quickly reaches a temperature of greater than 150 degree Celsius). In addition, other components of the picking instrument may need to be sterilized from time to time. Various sterilization techniques can be used, e.g., UV irradiation, bleach, and ethanol cleaning.

There are certain considerations that may help improve the picking efficiencies. For example, for a destination sample holder including wells containing a culture media, depositing the picked sample in the destination well can be done by leaving the distal tip of the pin in the culture media for an extended time, by advancing and retracting the picking pin through at least a portion of the culture media repeatedly (at the same or slightly different locations), and/or by dithering (laterally moving) the picking pin around while the distal tip is in the culture media. Additionally, keeping the samples contained in the microwells of the microfabricated chip hydrated can be beneficial in prolonged picking process. For example, a thin layer of oil can be dropped on top of the microwells of the chip to trap moisture on the chips. The oil is easy for the picking pin to go through.

It should be appreciated that a computer as described herein may be embodied in any of a number of forms, such as a rack-mounted computer, a desktop computer, a laptop computer, or a tablet computer. Additionally, a computer may be embedded in a device not generally regarded as a computer but with suitable processing capabilities, including a smart mobile phone, a tablet, or any other suitable portable or fixed electronic device. Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in another audible format. Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks. The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

What is claimed is:

1. A picking instrument, comprising:
   a picking pin having a distal tip and three degrees-of-freedom and configured to move in x, y, and z directions, the x, y directions constituting an x-y plane;
   a loading platform comprising a first area and a second area, the first area configured to accommodate and secure a microfabricated chip including a plurality of microwells;
   wherein the picking pin is operably connected to a computer, the computer including a computer program product that enables the determination of the coordinates of at least one selected microwell of the microfabricated chip on the x-y plane relative to a position of the picking pin based on a calibration of the position of the microfabricated chip relative to a position of the picking pin, and enables the picking pin to:
   move to a position above the at least one selected microwell in the plurality of the microwells of the microfabricated chip;
   pick a sample contained in the at least one selected microwell;
   move to a predetermined location at a destination sample holder; and
   transfer the picked sample to the predetermined location at the destination sample holder.

2. The picking instrument of claim 1, wherein the second area is configured to secure a destination sample holder having a plurality of wells that have greater dimensions than the microwells of the microfabricated chip.

3. The picking instrument of claim 1, wherein the second area is configured to secure another microfabricated chip having a plurality of microwells.

4. The picking instrument of claim 1, wherein the movement of the picking pin is driven by three programmatically controlled motors, each motor configured to move the picking pin in the x, y, and z direction independently, respectively.

5. The picking instrument of claim 4, wherein the picking pin is mounted on a spring.

6. The picking instrument of claim 1, further comprising a pressure sensor coupled with the picking pin, the pressure sensor being configured to sense an opposition force experienced by the picking pin when the distal tip of the picking pin contacts an object.

7. The picking instrument of claim 1, further comprising a camera configured to capture at least a portion of the microfabricated chip when it is loaded onto the loading platform.

8. The picking instrument of claim 1, wherein the camera is in a fixed spaced relationship with the loading platform.

9. The picking instrument of claim 1, further comprising an optical aligner configured to determine the coordinates of the picking pin.

10. The picking instrument of claim 9, wherein the optical aligner comprises a first light source, a first light detector, a second light source, and a second light detector, where the first light source and the first light detector are arranged such that a first light beam emitted from the first light source and received by the first light detector is along the y direction, and the second light source and the second light detector are arranged such a second light beam emitted from the second light source and received by the second light detector is along the x direction.

11. The picking instrument of claim 1, further comprising a sterilization device that is capable of sterilizing the distal tip of the picking pin.

12. The picking instrument of claim 1, further comprising a touchscreen for locating the coordinates of the picking pin.

13. The picking instrument of claim 1, wherein the loading platform is movably mounted on a rail structure.

\* \* \* \* \*